US008748593B2

(12) United States Patent
Gryaznov et al.

(10) Patent No.: US 8,748,593 B2
(45) Date of Patent: Jun. 10, 2014

(54) SYNTHESIS OF PROTECTED 3'-AMINO NUCLEOSIDE MONOMERS

(75) Inventors: Sergei M. Gryaznov, San Mateo, CA (US); Krisztina Pongracz, Oakland, CA (US); Daria Zielinska, Sunnyvale, CA (US)

(73) Assignee: Geron Corporation, Menlo Park, CA (US)

( * ) Notice: Subject to any disclaimer, the term of this patent is extended or adjusted under 35 U.S.C. 154(b) by 35 days.

(21) Appl. No.: 12/341,750

(22) Filed: Dec. 22, 2008

(65) Prior Publication Data

US 2009/0105468 A1 Apr. 23, 2009

Related U.S. Application Data

(62) Division of application No. 11/173,311, filed on Jun. 30, 2005, now Pat. No. 7,485,717.

(60) Provisional application No. 60/585,193, filed on Jul. 2, 2004.

(51) Int. Cl.
*C07H 19/167* (2006.01)
*C07H 19/173* (2006.01)
*C07H 21/00* (2006.01)

(52) U.S. Cl.
USPC .................................... 536/27.62; 536/27.81

(58) Field of Classification Search
None
See application file for complete search history.

(56) References Cited

U.S. PATENT DOCUMENTS 5,185,444 A 2/1993 Summerton et al.
5,476,925 A 12/1995 Letsinger et al.
5,591,607 A 1/1997 Gryaznov et al.
5,599,922 A 2/1997 Gryaznov et al.
5,631,135 A 5/1997 Gryaznov et al.
5,646,260 A 7/1997 Letsinger et al.
5,648,480 A 7/1997 Letsinger et al.
5,684,143 A 11/1997 Gryaznov et al.
5,726,297 A 3/1998 Gryaznov et al.
5,824,793 A 10/1998 Hirschbein et al.
5,837,835 A 11/1998 Gryaznov et al.
5,859,233 A 1/1999 Hirschbein et al.
5,932,718 A 8/1999 Letsinger et al.
5,965,720 A 10/1999 Gryaznov et al.
5,998,604 A 12/1999 Fearon et al.
6,169,170 B1 1/2001 Gryaznov et al.
6,608,036 B1 8/2003 Gryaznov et al.
6,835,826 B2 12/2004 Gryaznov et al.
7,138,383 B2 11/2006 Gryaznov et al.
7,494,982 B2 2/2009 Gryaznov et al.
7,563,618 B2 7/2009 Gryaznov et al.

FOREIGN PATENT DOCUMENTS

WO WO 97/31009 8/1997
WO WO 01/18015 3/2001
WO WO 02/077184 10/2002
WO WO 2004/029277 4/2004
WO WO 2005/023994 3/2005

OTHER PUBLICATIONS

Kates et al. Solid-Phase Synthesis, A Practical Guide, Marcel Dekker, Inc. 2000, pp. 478-480.*

Greene. Protective Groups in Organic Synthesis, Third Edition, John Wiley & Sons, Inc. 1999, p. 588.*

Chapuis et al. Tetrahedron 62 (2006) 12108-12115.*

PCT search report for PCT/US2005/023633, 2 pages (Jan. 19, 2006).

Baraniak, J. et al., "New approach to solid phase synthesis of N3'-P5' phosphoramidate oligonucleotides," *Nucleosides & Nucleotides* 17(8):1347-53 (1998).

Froehler, B. & Matteucci, M., "Dialkylformamidines: depurination resistant N6-protecting group for deoxyadenosine," *Nucl. Acids Res.* 11(22):8031-6 (1983).

Greene, T. & Wuts, P., "Protection for the hydroxyl group, including 1,2- and 1,3-diols," *Protective Groups in Organic Synthesis*, Third Edition, John Wiley & Sons, Inc., New York, pp. 17-23, 494-502 (1999).

Greene, T. & Wuts, P., *Protective Groups in Organic Synthesis*, Third Edition, John Wiley & Sons, Inc., New York, pp. 4-5, 119, 142-3, 513, 550, 559, 583-4 (1999).

Gryaznov, S. & Winter, H., "RNA mimetics: oligoribonucleotide N3'-P5' phosphoramidates," *Nucl. Acids Res.* 26(18):4160-7 (1998).

Liekens, S. et al., "The nucleoside derivative 5'-O-trityl-inosine (KIN59) suppresses thymidine phosphorylase-triggered angiogenesis via a noncompetitive mechanism of action," *J. Biol. Chem.* 279(28):29598-605 (2004).

Matray, T. & Gryaznov, S., "Synthesis and properties of RNA analogs—oligoribonucleotide N3'-P5' phosphoramidates," *Nucl. Acids Res.* 27(20):3976-85 (1999).

Mignet, N. & Gryaznov, S., "Zwitterionic oligodeoxyribonucleotide N3'→P5' phosphoramidates: synthesis and properties," *Nucl. Acids Res.* 26(2):431-8 (1998).

Nakajima, K. et al., "Studies on aziridine-2-carboxylic acid. I. Synthesis of the optically active L-aziridine-2-carboxylic acid and its derivatives," *Bull. Chem. Soc. Jpn.* 51:1577-8 (1978).

Nelson, J. et al., "N3'-P5' oligodeoxyribonucleotide phosphoramidates: a new method of synthesis based on a phosphoramidate amine-exchange reaction," *J. Org. Chem.* 62:7278-87 (1997).

(Continued)

*Primary Examiner* — Layla Bland
(74) *Attorney, Agent, or Firm* — Leslie A. Mooi

(57) ABSTRACT

Orthogonally protected 3'-amino nucleoside monomers and efficient methods for their synthesis are described. The methods employ selective protection of the 3'-amino group in the presence of the unprotected nucleoside base.

7 Claims, 5 Drawing Sheets

(56) References Cited

OTHER PUBLICATIONS

Pongracz, K. & Gryaznov, S., "Oligonucleotide N3'→P5' thiophosphoramidates: synthesis and properties," *Tetrahedron Lett.* 40:7661-4 (1999).
Pongracz, K. & Gryaznov, S., "α-Oligodeoxyribonucleotide N3'→P5' phosphoramidates: synthesis and duplex formation," *Nucl. Acids Res.* 26(4):1099-106 (1998).
TI, G. et al., "Transient protection: efficient one-flask syntheses of protected deoxynucleosides," *J. Am. Chem. Soc.* 104:1316-9 (1982).
Zhang, B. et al., "Synthesis of pCpCpA-3'-NH-phenylalanine as a ribosomal substrate," *Org. Lett.* 4(21):3615-8 (2002).
Zhang, L. et al., "An efficient synthesis of 3'-amino-3'-deoxyguanosine from guanosine," *Helvetica Chimica Acta* 86:703-10 (2003).

* cited by examiner

SYNTHESIS OF PROTECTED 3'-AMINO NUCLEOSIDE MONOMERS

This application is a divisional of U.S. application Ser. No. 11/173,311, filed Jun. 30, 2005, now U.S. Pat. No. 7,485,717, which claims priority to U.S. Provisional Appl. No. 60/585,193, filed Jul. 2, 2004, both of which are hereby incorporated herein by reference in their entirety.

FIELD OF THE INVENTION

The present invention relates to efficient methods of synthesis of orthogonally protected 3'-amino nucleoside monomers, useful for the synthetic preparation of oligonucleotide analogs, and to the orthogonally protected monomers prepared by such methods.

REFERENCES

Asai, A. et al., *Cancer Research* 63(14):3931-9 (2003).
Carpino, L. A. et al., *J. Org. Chem.* 45:4250-2 (1980).
Carpino, L. A. et al., *J. Org. Chem.* 54:5887-97 (1989).
Cech, D. et al., *Coll. Czech. Chem. Comm.* 61:S297-S300 (1996).
Chen, J.-K., Schultz, R. G., Lloyd, D. H. and Gryaznov, S. M., *Nucleic Acids Res.* 23: 2661-2668 (1994).
Escude, C., Giovannageli, C., Sun, J.-S., Lloyd, D.-H., Chen, J.-K., Gryaznov, S. M., Garestier, T. and Helene, C., *Proc. Natl. Acad. Sci. USA* 93:4365-4369 (1996).
Giovannangeli, C., Diviacco, S., Labrousse, V., Gryaznov, S. M., Charneau, P. and Helene, C., *Proc. Natl. Acad. Sci. USA* 94:79-84 (1997).
Gryaznov, S. M. and Chen, J.-K. *J. Am. Chem. Soc.* 116:3143-3144 (1994).
Gryaznov, S. M. et al., *Nucleosides, Nucleotides & Nucleic Acids* 22(5-8):577-581 (2003).
Gryaznov, S. M., Lloyd, D. H., Chen, J.-K., Schultz, R. G., DeDionisio, L. A., Ratmeyer, L. and Wilson, W. D., *Proc. Natl. Acad. Sci. USA* 92:5798-5802 (1995).
Gryaznov, S. M., Pongracz, K., and Matray, T., PCT Pubn. No. WO 2001/018015 (Mar. 15, 2001).
Gryaznov, S. M., Skorski, T., Cucco, C., Nieborowska-Skorska, M, Chiu, C. Y., Lloyd, D. H., Chen, J. K., Koziolkiewicz, M. and Calabretta, B. *Nucleic Acids Res.* 24:1508-1514 (1996).
Nelson, J. S. et al., *J. Org. Chem.* 62:7278-7287 (1997).
Pongracz, K. and Gryaznov, S. M., *Tetrahedron Letters* 40(43): 7661-7664 (1999).
Skorski, T., Perrotti, D., Nieborowska-Skorska, M., Gryaznov, S. M. and Calabretta, B., *Proc. Natl. Acad. Sci. USA* 94:3966-3971 (1997).
Vincente, S. et al., *J. Org. Chem.* 64:991-997 (1999).
Vu, H. et al., *Tetrahedron Letters* 31(5):7269-7272 (1990).
Wang, E. S. et al., *Blood* 103(1):258-266 (2004).
Zaitseva, G. V. et al., *Nucleosides & Nucleotides* 13(1-3):819-838 (1994).
Zaitseva, V. E. et al., Sov. *J. Bioorg. Chem.* 10(5)5:369-378 (transl. from *Bioorg. Khim.* 10(5):670-680) (1984).

BACKGROUND OF THE INVENTION

The use of oligonucleotides and oligonucleotide analogs as therapeutic agents, based on specific binding to target nucleic acid sequences or to proteins, has been extensively researched. Structurally modified oligonucleotide analogs have been designed which lack the nuclease susceptibility of natural (phosphodiester-linked) oligonucleotides and which, in some cases, exhibit other beneficial properties such as enhanced binding to targets or enhanced specificity of binding. One such class of oligonucleotide analog is the N3'→P5' phosphorodiamidate-linked oligonucleotide (Gryaznov and Chen, 1994; Chen et al., 1994). These compounds are nuclease resistant, form stable duplexes with complementary RNA and duplex DNA targets, and have demonstrated significant sequence-specific antisense activity both in vitro and in vivo (Gryaznov et al., 1995; Escude et al., 1996; Gryaznov et al., 1996; Giovannangeli et al., 1997; Skorski et al., 1997). The related N3'→P5' thiophosphoramidate oligonucleotides retain the high RNA binding affinity of N3'→P5' phosphoramidates and also exhibit improved acid stability (Pongracz and Gryaznov, 1999; Gryaznov et al., 2001). Certain N3'→P5' thiophosphoramidate oligonucleotides have shown therapeutically promising telomerase inhibiting activity (Gryaznov et al., 2003; Asai et al., 2003; Wang et al., 2004).

Stepwise, sequence-controlled preparation of N3'→P5' phosphoramidate or thiophosphoramidate oligonucleotides employs 3'-amino nucleoside monomers in which the 3'-amino group is protected during addition, then deprotected for addition of a further monomer to the growing oligonucleotide chain (see e.g. Gryaznov and Chen, 1994; Pongracz and Gryaznov, 1999). Because the groups on the nucleoside bases which are typically protected during synthesis are primary amino groups, the need for protection of the 3'-amino group in the presence of these groups has complicated the preparation of these monomers. Existing procedures (see e.g. Nelson et al., 1997) entail multiple steps of protection and generally involve conversion of a 3'-hydroxyl to a 3'-azido ($-N_3$) group, which is later reduced to the 3'-amine. These procedures are time consuming, expensive, and result in low overall yields of the monomers. Accordingly, improving the efficiency of these syntheses is desired, and will facilitate the preparation of N3'→P5' phosphoramidate or thiophosphoramidate oligonucleotides.

SUMMARY OF THE INVENTION

The present invention provides, in one aspect, a method of preparing an adenosine, guanosine or cytidine monomer having a protected nucleoside base and a protected 3'-amino group, wherein the base and the 3'-amino group are orthogonally protected. In one embodiment, the method comprises the steps of:

(a) providing a 3'-amino-3'-deoxy adenosine, cytidine, or guanosine monomer in which the 5'-hydroxyl group, nucleoside base, and 3'-amino group are unprotected;

(b) selectively reacting the 3'-amino group with a first protecting group;

reacting the 5'-hydroxyl group with a second protecting group; and reacting the nucleoside base with a third protecting group;

wherein the first protecting group can be removed from the 3'-amino group under conditions which do not deprotect the nucleoside base, and the second protecting group can be removed from the 5'-hydroxyl group under conditions which do not deprotect the nucleoside base or the 3'-amino group. The method may further comprise the step of (c) removing the second protecting group from the 5'-hydroxyl group, under conditions which do not deprotect the nucleoside base or the 3'-amino group.

The first protecting group may be acid labile; e.g. a triarylmethyl group, such as triphenylmethyl(trityl), monomethoxytrityl (MMT), or dimethoxytrityl (DMT). In another embodiment, the first protecting group is fluorenylmethoxycarbonyl (Fmoc) or a derivative thereof, removable with a basic amine such as DBU or piperidine.

In one embodiment, preferably employed for an adenosine or cytosine monomer, the second and third protecting groups are both acyl groups, e.g. benzoyl groups, and the conditions of (c) comprise mild treatment with hydroxide ion.

In another embodiment, the second protecting group is a base labile trialkyl silyl ether, e.g. a trimethylsilyl (TMS) ether, the third protecting group is an acyl group, and the conditions of (c) comprise mild treatment with hydroxide ion.

In a further embodiment, the second protecting group is a fluoride labile silyl ether, the third protecting group is an acyl group, and the conditions of (c) comprise treatment with fluoride ion. Such fluoride labile silyl ethers include, for example, a tert-butyldimethyl silyl ether, a tert-butyldiphenyl silyl ether, a diphenylmethyl silyl ether, and a tri(isopropyl) silyl ether. In one embodiment, the fluoride labile silyl ether is a tert-butyldimethyl silyl (TBDMS) ether.

In an alternative embodiment, the method comprises the steps of:

(a) providing a 3'-amino-3'-deoxy adenosine, cytidine, or guanosine monomer in which the 5'-hydroxyl group, nucleoside base, and 3'-amino group are unprotected;

(b) selectively reacting the 3'-amino group with a first protecting group; and selectively reacting the nucleoside base with a further protecting group;

wherein the first protecting group can be removed from the 3'-amino group under conditions which do not deprotect the nucleoside base.

In this embodiment of the method, the 5'-OH group remains substantially unreacted under conditions of protection of the nucleoside base, and does not require separate protection. In one embodiment, the monomer is a cytidine monomer, the first protecting group is as described above, and the further protecting group is an acyl group, preferably a benzoyl group. The acyl protecting group is preferably incorporated by means of reaction with an acyl anhydride.

In other embodiments, the monomer is a guanosine or adenosine monomer, the first protecting group is as described above, and the further protecting group is a formamidinyl group, such as a dialkylformamidinyl group.

In a related aspect, the invention provides a method of preparing a thymidine monomer having a free 5'-hydroxyl group and a protected 3'-amino group, the method comprising:

(a) providing a 3'-amino-3'-deoxy thymidine monomer in which the 5'-hydroxyl group and 3'-amino group are unprotected; and (b) selectively reacting the 3'-amino group with a first protecting group.

The first protecting group may be acid labile; e.g. a triarylmethyl group, such as triphenylmethyl(trityl). In another embodiment, the first protecting group is fluorenylmethoxycarbonyl (Fmoc) or a derivative thereof, removable with a basic amine such as DBU or piperidine.

The starting and product monomers in these synthetic methods preferably comprise a 2' group selected from hydrogen, hydroxy, lower alkoxy, lower alkyl, and fluoro. In selected embodiments, the monomer comprises a 2' group selected from hydrogen, hydroxy, methoxy, and fluoro. In one embodiment, the monomer is a 2',3'-dideoxy monomer, such that the 2' group is hydrogen.

In another aspect, the invention provides an adenosine, guanosine, or cytidine monomer having a protected 3'-amino group and a nucleoside base which is (i) unprotected or (ii) protected such that the protected 3'-amino group can be deprotected under conditions which do not deprotect the nucleoside base. In selected embodiments, the 3'-amino group is protected with an acid labile protecting group; e.g. a triarylmethyl group, such as triphenylmethyl(trityl). In other embodiments, the 3'-amino group is protected with fluorenylmethoxycarbonyl (Fmoc) or a derivative thereof which is removable with a basic amine such as DBU or piperidine.

In one embodiment, the nucleoside base is unprotected; in other embodiments, the nucleoside base is protected with an acyl group. Preferably, the acyl group is benzoyl when the monomer is an adenosine or cytidine monomer and isobutyryl when the monomer is a guanosine monomer. In still further embodiments, the nucleoside base is protected with a formamidinyl group, preferably a nucleoside base is protected with a dialkylformamidinyl group.

The 5'-hydroxyl group of the monomer may be unprotected, or it may be protected such that it can be deprotected under conditions which do not deprotect the nucleoside base or the 3'-amino group. For example, it may be protected with a silyl ether which is labile to mild base of to fluoride ion, such as those noted above.

The monomer preferably comprises a 2' group selected from hydrogen, hydroxy, lower alkoxy, lower alkyl, and fluoro. In selected embodiments, the monomer comprises a 2' group selected from hydrogen, hydroxy, methoxy, and fluoro. In one embodiment, the monomer is a 2',3'-dideoxy monomer, such that the 2' group is hydrogen.

These and other objects and features of the invention will become more fully apparent when the following detailed description of the invention is read in conjunction with the accompanying drawings.

DETAILED DESCRIPTION OF THE INVENTION

I. Definitions

Figure 1:
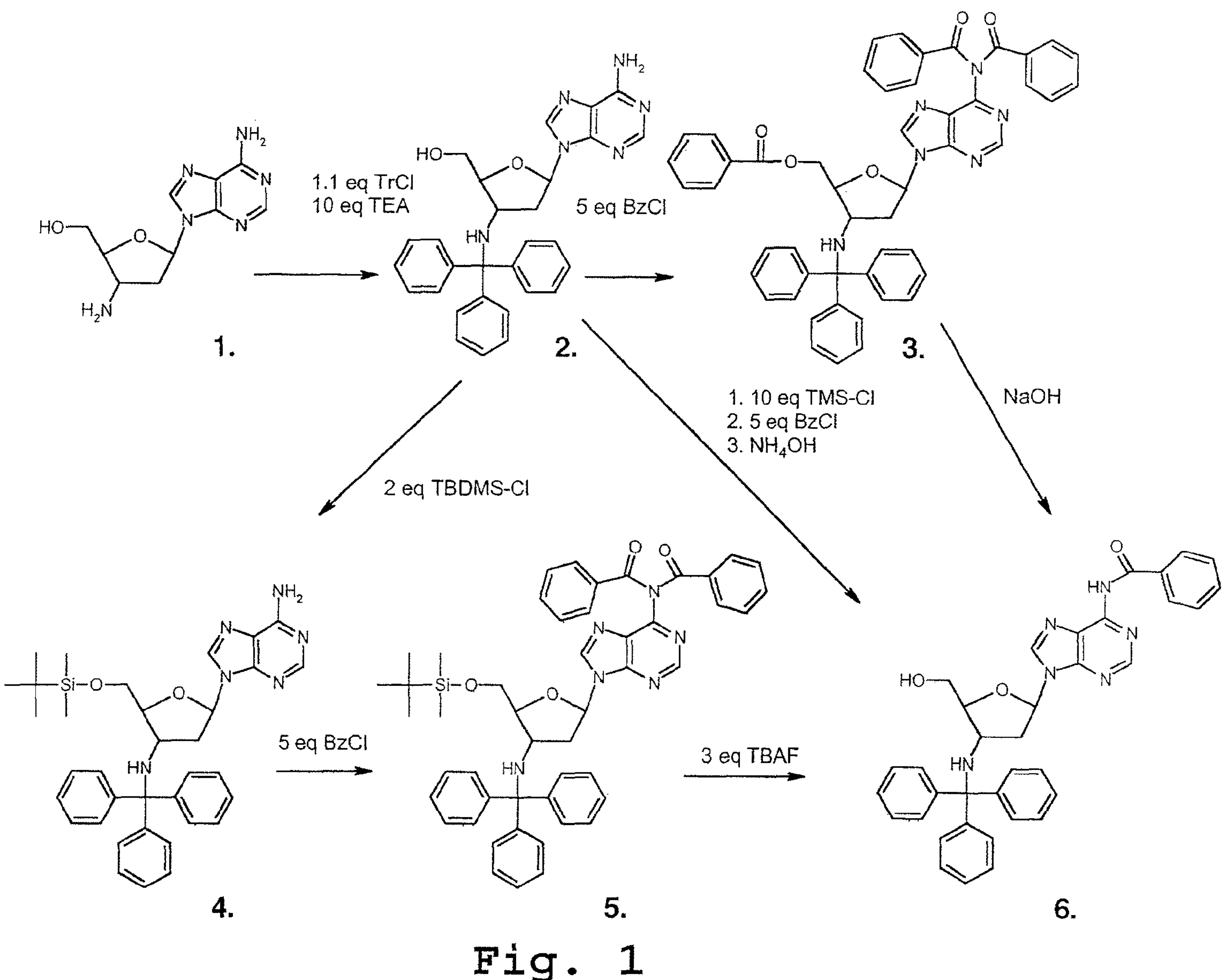
FIG. 1 is a scheme showing alternative exemplary methods for synthesis of a 3'-amino adenosine monomer, also applicable for synthesis of 3'-amino cytidine monomers, in accordance with various embodiments of the invention.

The terms below have the following meanings unless indicated otherwise.

"Orthogonally protected", with respect to a plurality of protected functional groups in the same molecule, indicates that it is possible to deprotect any selected member of the group without deprotecting the other group(s).

"Selectively protected", with respect to protection of a target functional group in a molecule having a plurality of unprotected functional groups, indicates that, in a reaction of the molecule with a protecting reagent, the target functional group is protected to a greater extent than any non-target functional group. The extent of reaction of the target functional group relative to that of any non-target functional group(s) is greater than 1:1, preferably greater than 2:1, and more preferably greater than 3:1 or higher, e.g. greater than 9:1. The same definition applies to the terminology "selectively reacting" a given functional group with a protecting group.

"Reacting with a protecting group", as used herein, is equivalent to "providing with a protecting group", "protecting with a protecting group", or "reacting with a protecting group reagent".

"Alkyl" refers to a fully saturated acyclic moiety consisting of carbon and hydrogen, which may be linear or branched. Examples of alkyl groups are methyl, ethyl, n-butyl, t-butyl, n-heptyl, and isopropyl. Generally preferred are lower alkyl groups, having one to six carbon atoms, as exemplified by methyl, ethyl, n-butyl, i-butyl, t-butyl, isoamyl, n-pentyl, and isopentyl. In other embodiments, lower alkyl includes groups having one to four carbon atoms, or 1-2 carbon atoms (methyl and ethyl).

"Cycloalkyl" refers to a saturated cyclic hydrocarbon, preferably having 4 to 7 carbon atoms, more preferably 5 or 6 (i.e. cyclopentyl or cyclohexyl).

"Alkenyl" refers to an unsaturated acyclic moiety consisting of carbon and hydrogen, which may be linear or branched, having one or more double bonds. Generally preferred are lower alkenyl groups, having two to six, or two to four, carbon atoms. "Alkynyl" refers to an unsaturated acyclic moiety consisting of carbon and hydrogen, which may be linear or branched, containing one or more triple bonds. Generally preferred are lower alkynyl groups, having two to six, or two to four, carbon atoms.

"Aryl" refers to a substituted or unsubstituted monovalent aromatic radical, generally having a single ring (e.g., benzene) or two condensed rings (e.g., naphthyl), where monocyclic aryl groups are preferred. The term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group, preferably one or two ring hydrogens, is replaced with a group preferably selected from fluorine, chlorine, bromine, methyl, ethyl, methoxy, halomethoxy, and halomethyl. Preferred aryl groups for use in protecting groups are carbocyclic aryls which are unsubstituted or substituted with lower alkoxy (in addition to the substituent linking the group to the protected moiety).

"Aralkyl" refers to an alkyl, preferably lower ($C_1$-$C_4$, more preferably $C_1$-$C_2$) alkyl, substituent which is further substituted with an aryl group, preferably a monocyclic aryl group; examples are benzyl ($—CH_2C_6H_5$) and phenethyl.

"Acyl" refers to a substituent of the form R(C═O)—, where R is alkyl, alkenyl, alkynyl, aralkyl, or aryl as defined above, and is preferably selected from lower alkyl and monocyclic carbocyclic aryl. Examples include benzoyl (Ph(C═O)—), acetyl ($CH_3$(C═O)—) and isobutyryl ($(CH_3)_2$CH(C═O)—).

II. Synthesis of Protected Monomers

The invention provides, in one aspect, efficient syntheses of orthogonally protected 3'-amino-5'-hydroxyl nucleoside monomers, in which the amino groups on the 3'-position and the nucleoside base are orthogonally protected, starting from the corresponding unprotected 3'-amino nucleosides. Typically, the product monomers are then phosphitylated at the free 5'-hydroxyl for use in synthesis of N3'→P5' phosphoramidate or thiophosphoramidate oligonucleotides. (See e.g. FIG. 2B and FIG. 3.)

A. Starting Materials

The starting material for the monomer synthesis is a 3'-amino nucleoside having the general formula below:

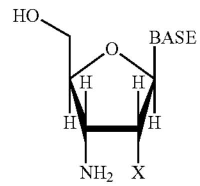

where BASE is an unprotected nucleoside base selected from guanine (G), adenine (A), thymine (C) and cytosine (C). The 2'-substituent X may be hydrogen, as in 2',3'-dideoxy monomers, for producing DNA analogs. Alternatively, X may be hydroxy or lower alkoxy, such as methoxy, for producing RNA or O-alkyl RNA analogs. The 2'-substituent may also be fluorine (see e.g. U.S. Pat. No. 5,684,143) or lower alkyl, such as methyl.

The 3'-amino-2',3'-dideoxy nucleosides, useful as starting materials in the syntheses herein, can be obtained commercially from Metkinen Oy, located in Littoinen, Finland. The 3'-amino-2',3'-dideoxy thymidine starting material is also commercially available from various sources such as Dalton Chemical Labs (Toronto, Canada) and MP Biomedicals Inc. (Irvine, Calif.). Various synthetic preparations of the 3'-amino-2',3'-dideoxy nucleosides have been reported in the literature (e.g. Zaitseva et al., 1994; Cech et al., 1996; Zaitseva et al., 1984). In accordance with Zaitseva et al., 1994, 3'-amino-2',3'-dideoxy thymidine can be converted into the corresponding adenosine or guanosine monomers via enzymatic transglycosylation.

B1. Protection Strategies: Overview

In accordance with the invention, efficient procedures are provided for converting the above-depicted nucleosides into the corresponding base-protected (in the case of A, G, and C), 3'-amino-protected monomers. Because the groups on the bases which must be protected are also amino groups, selective protection of the 3'-amino group in the presence of the unprotected base, or vice versa, has not been carried out successfully in the past, and existing procedures for the preparation of these monomers (see e.g. Nelson et al., 1997) entail multiple steps of protection and generally involve conversion of a 3'-hydroxyl to an azido group, which is later reduced to the 3'-amine.

The present inventors have provided efficient methods for selectively protecting the 3'-amino group in the presence of the nucleoside bases, such that the nucleoside base can then be protected with an orthogonal protecting group; that is, one that is not removed under selected conditions that are effective to remove the 3'-amino protecting group (or the 5'-hydroxyl protecting group, if present).

In addition, the 3'-amino group is also selectively protected in the presence of the 5'-hydroxyl group, or vice versa. Accordingly, it is possible to provide the free 5'-hydroxyl with a protecting group, which can be removed under selected conditions which do not remove either the 3'-amino protecting group or the base protecting group. (Alternatively, as in the case of thymidine, the free 5'-hydroxyl can be directly phosphitylated.)

The protecting group for the 5'-hydroxyl may be, for example, a silyl group, which can be removed under conditions, such as mild base or fluoride ion, which do not remove the protecting groups (typically acyl or amidinyl groups) used for the nucleotide base. Alternatively, the same protecting group (such as an acyl group) can be used for the 5'-hydroxyl and nucleotide base, with conditions employed for its removal (e.g. mild base) that will deprotect the hydroxyl group but not the nucleotide base amino groups.

In a further strategy, the nucleotide base can be protected under conditions that leave the 5'-hydroxyl unreacted, and thus not requiring protection.

In all cases, the protecting groups employed for the nucleotide bases are stable to the conditions of monomer coupling reactions employed in oligonucleotide synthesis. Methods for preparing N3'→P5' phosphoramidate or thiophosphoramidate oligonucleotides from the monomers described herein are described, for example, in Gryaznov and Chen (1994) and Pongracz and Gryaznov (1999).

B2. Protection Strategies: A, G, and C Monomers

The invention provides, for adenosine, guanosine, or cytidine monomers, methods of preparing said monomers having a free 5'-hydroxyl group, a protected nucleoside base, and a protected 3'-amino group, where the base and 3'-amino group are orthogonally protected, as defined above. The starting material is a 3'-amino-3'-deoxy adenosine, cytidine, or guanosine monomer in which the 5'-hydroxyl group, nucleoside base, and 3'-amino group are unprotected.

In one general strategy, the method comprises selectively reacting the 3'-amino group with a first protecting group, reacting the 5'-hydroxyl group with a second protecting group, and reacting the nucleoside base with a third protecting group. The first protecting group (for the 3'-amino) is such that it can be removed from the 3'-amino group under conditions which do not deprotect the nucleoside base. Moreover, the second protecting group (for the 5'-hydroxyl), when present, is such that it can be removed from the 5'-hydroxyl group under conditions which do not deprotect the nucleoside base or the 3'-amino group.

After the desired reactive groups are protected, in accordance with the above general strategy, the second protecting group, if present, is removed from the 5'-hydroxyl group, under conditions which do not deprotect the nucleoside base or the 3'-amino group. The monomer can then be phosphitylated, e.g. for use in oligonucleotide synthesis.

Typically, the first, second, and third protecting groups are applied in that order, although the second and third groups may in fact be the same, and thus applied in a single reaction. Moreover, protection of the 5'-hydroxyl group, in strategies employing this step, can occur before or after the protection of the 3'-amino group. The two reactions are typically carried out in a one-pot reaction, although the reagents are preferably not added simultaneously. Preferably, the 3'-amino protecting reagent is added first, as illustrated in the examples below.

In selected embodiments, transient protection of the 5'-hydroxyl group with a base labile silyl ether (e.g. TMS) is employed during the base protection step, as shown, for example, in FIG. 1 (conversion of structure 2 to structure 6) and in FIG. 2B, as discussed further below.

In other embodiments, the 5'-hydroxyl group and nucleotide bases are protected with the same reagent, followed by selective deprotection of the hydroxyl group. Such a reagent is typically an acylating reagent, e.g. an isobutyryl halide or benzoyl halide. An exemplary scheme of this type is shown in the conversion of structure 2 to 3 in FIG. 1, followed by treatment with base under mild conditions to selectively deprotect the hydroxyl group (conversion of 3 to 6).

As noted above, the first protecting group, for protecting the 3'-amine, is one that is stable under conditions that can remove the second protecting group (for the 5'-hydroxyl), when present, but is labile under conditions that do not remove the third protecting group (for the nucleoside base). In one embodiment, the first protecting group is acid labile; e.g. a triarylmethyl group such as trityl(triphenylmethyl), monomethoxytrityl (MMT), or dimethoxytrityl (DMT).

Another group useful as the first protecting group is fluorenylmethoxycarbonyl (Fmoc), which is removable via non-hydrolytic cleavage with a basic amine, such as DBU, morpholine, or piperidine. A hydroxide base (e.g. NaOH) is not suitable for this purpose, since this reagent will typically remove other protecting groups in the molecule as well. Derivatives of Fmoc which are removable by a similar mechanism may also be used. Such derivatives include those in which the fluorenyl group of Fmoc is substituted, typically at the 2 and/or 7 position, with a group, such as a lower alkyl group, which will not impact the cleavage mechanism, or with an electron withdrawing group, such as halogen, which increases the base lability of the protecting group (Carpino et al., 1980). Also included are the thioxanthene dioxide analogs described in Carpino et al., 1989.

Figure 2A:
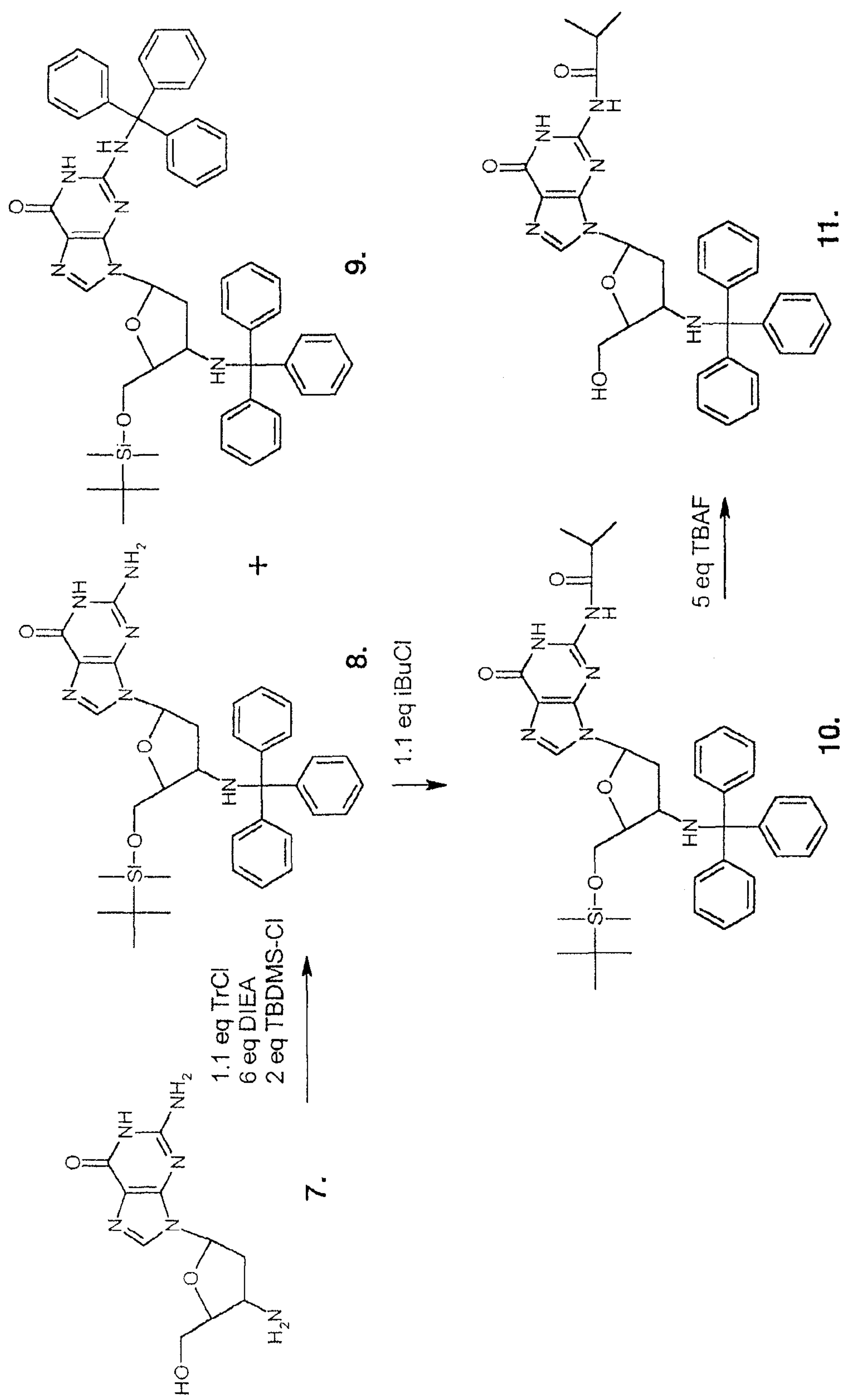
FIG. 2A shows an exemplary method for synthesis of a 3'-amino guanosine monomer, in accordance with one embodiment of the invention.

FIG. 1 shows exemplary permutations of a synthetic strategy which can be used for preparation of the subject monomers. These methods are particularly suitable for A (adenosine) and C (cytidine) nucleoside monomers. As described below, the methods can also be used, preferably with some modifications, for G (guanosine) monomers. In the strategies exemplified in FIGS. 1 and 2A-B, protection of the 5'-hydroxy is employed. FIG. 2C, discussed further below, illustrates a strategy in which 5'-hydroxy protection is not employed.

As noted above, a preferred first protecting group (for the 3'-amine) is an acid labile group, such as trityl, MMT, or DMT, or a group, such as Fmoc, which is labile to a basic amine reagent such as DBU. In one embodiment, preferred second and third protecting groups are both aracyl groups, e.g. benzoyl groups. Conditions which are effective to deprotect the 5'-hydroxyl group under conditions which do not deprotect the nucleoside base or the 3'-amino group, in this case, preferably comprise mild base treatment, such as treatment with hydroxide, e.g. ammonium hydroxide. Such treatment is effective to remove the acyl group from the 5'-hydroxyl and to convert diacylated base to monoacylated base. Such as scheme is illustrated in FIG. 1, in the conversion of intermediate 3 to product 6.

In another embodiment, the second protecting group, for protection of the 5'-hydroxyl, is a base labile trialkyl silyl ether, preferably TMS, and the third protecting group (for protection of the nucleotide base) is an acyl group, such as an alkanoyl, preferably isobutyryl, or benzoyl group. Again, conditions which are effective to deprotect the 5'-hydroxyl group under conditions which do not deprotect the nucleoside base or the 3'-amino group, in this case, preferably comprise mild base treatment, e.g. treatment with hydroxide. Such treatment is effective to cleave a trimethylsilyl ether and to convert diacylated base, if present, to monoacylated base. An example of this scheme is also illustrated in FIG. 1, in the conversion of intermediate 2 to product 6.

Another preferred type of nucleotide base protecting group, particularly for adenosine and guanosine monomers, is a formamidinyl protecting group, such as a dialkyl-, di(cycloalkyl)-, or di(aralkyl)-formamidinyl group, where "alkyl" is preferably $C_1$-$C_4$ and "cycloalkyl" is preferably $C_5$-$C_6$. Specific examples include dimethylformamidinyl and dibenzylformamidinyl. These protecting groups can generally be removed from the nucleotide bases (e.g. at the end of synthesis) under milder conditions than are used to remove benzoyl or isobutyryl protecting groups. See, for example, Vu et al., 1990, Vincent et al., 1999, and/or U.S. Pat. No. 5,281,701. As described therein, reaction of a primary amine with a dialkylformamide dimethyl acetal, for example, provides the dialkylformamidinyl-protected amine. Deprotection can generally be effected by treatment with aqueous or alcoholic ammonium hydroxide at room temperature to about 55° C.

In a further embodiment, the second protecting group (for protecting the 5'-hydroxyl) is a fluoride-labile silyl ether, and the third protecting group (for the nucleoside base) is an acyl group, such as a benzoyl group, or a formamidinyl group as described above. In this case, conditions which are effective to deprotect the 5'-hydroxyl group, under conditions which do not deprotect the nucleoside base or the 3'-amino group, preferably comprise treatment with fluoride ion, e.g. tetrabutylammonium fluoride (TBAF). Such treatment is effective to cleave the silyl ether and to convert diacylated base, if present, to monoacylated base. An example of this scheme is also illustrated in FIG. 1, in the conversion of intermediate 5 to product 6. Exemplary fluoride-labile silyl ethers include, for example, tert-butyldimethyl silyl ether, tert-butyldiphenyl silyl ether, diphenylmethyl silyl ether, tri(isopropyl) silyl ether, and others known in the art.

The above methods can also be used, with some modifications relating primarily to solubility, for guanosine (G) monomers. In one embodiment, illustrated in FIG. 2A, the 5'-hydroxyl group of the starting monomer 7 is protected with a lipophilic group, such as TBDMS, at an early stage of the process, to facilitate solubility in the conventional solvent pyridine.

As noted above, a preferred first protecting group (for the 3'-amine) is an acid labile group, such as trityl, DMT, or MMT, or a group, such as Fmoc, which is labile to a basic amine reagent such as DBU. A trityl group is employed in the embodiment of FIG. 2A.

Depending on reaction conditions, small quantities (e.g. about 5%) of the ditritylated compound 9 may be observed in addition to the desired 3'-monotritylated compound 8. Accordingly, "selective protection" as used herein indicates that the molecule having the desired state of protection is formed to a greater extent, i.e. in a ratio greater than 1:1, than molecules in which non-target functional groups are protected, either exclusively or in addition to the target functional group. Preferably, the ratio is greater than 2:1, more preferably greater than 3:1, and most preferably greater than 9:1.

The second protecting group (for the 5'-hydroxyl) is, in this embodiment, a fluoride-labile silyl ether, and more preferably a group which promotes solubility of the intermediate. A TBDMS ether, as shown in FIG. 2A, was found to promote solubility in the solvent pyridine.

The third protecting group is preferably an acyl group, e.g. an isobutyryl group, or a formamidinyl group as described above. Conditions which are effective to deprotect the 5'-hydroxyl group, under conditions which do not deprotect the nucleoside base or the 3'-amino group, preferably comprise treatment with fluoride ion, e.g. tetrabutylammonium fluoride (TBAF). Such treatment is effective to cleave the silyl ether in compound 10 without affecting isobutyryl or trityl groups, as shown in FIG. 2A.

Figure 2B:
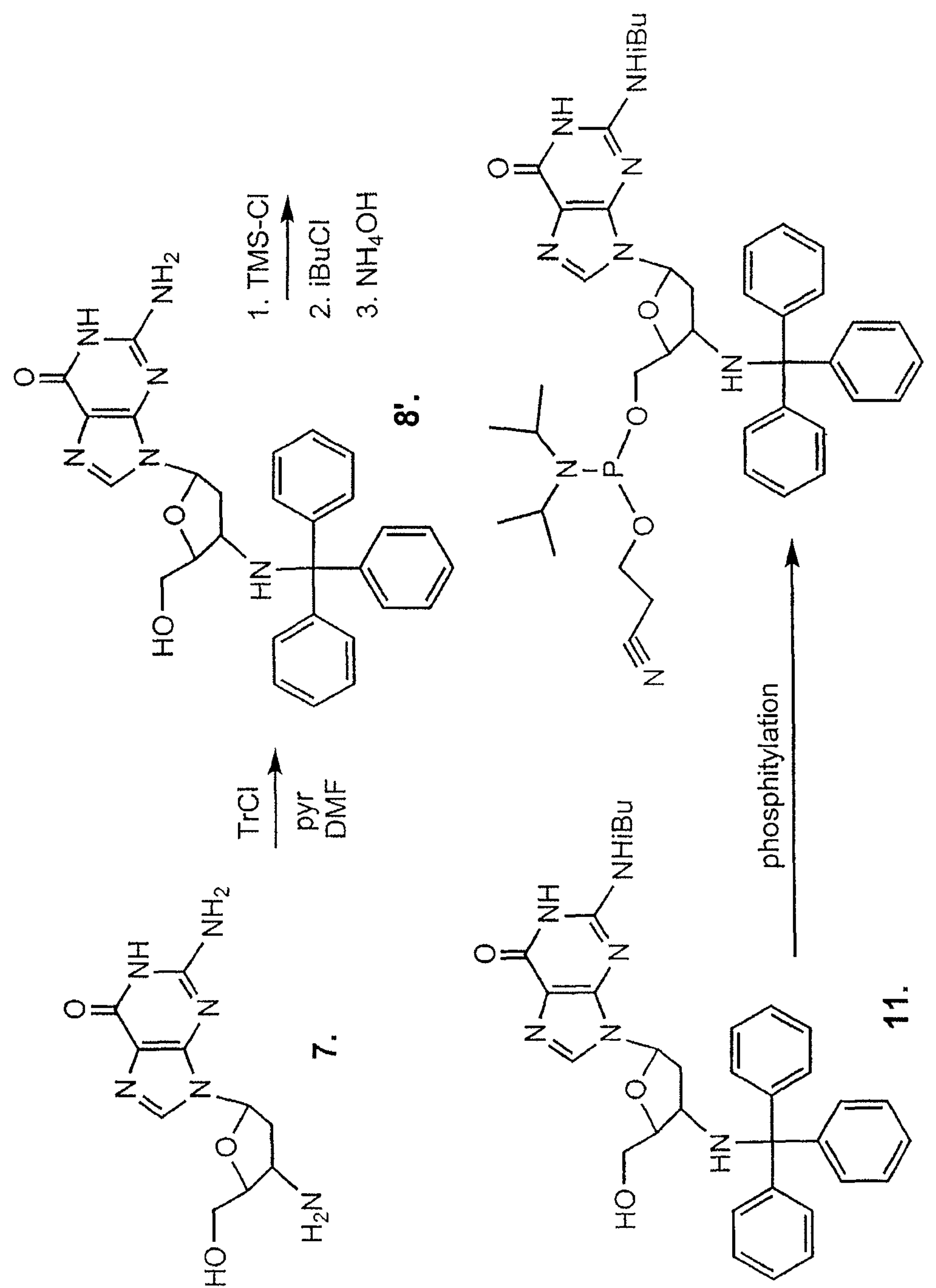
FIG. 2B shows an alternative exemplary method for synthesis of a 3'-amino guanosine monomer, in accordance with one embodiment of the invention.
Figure 2C:
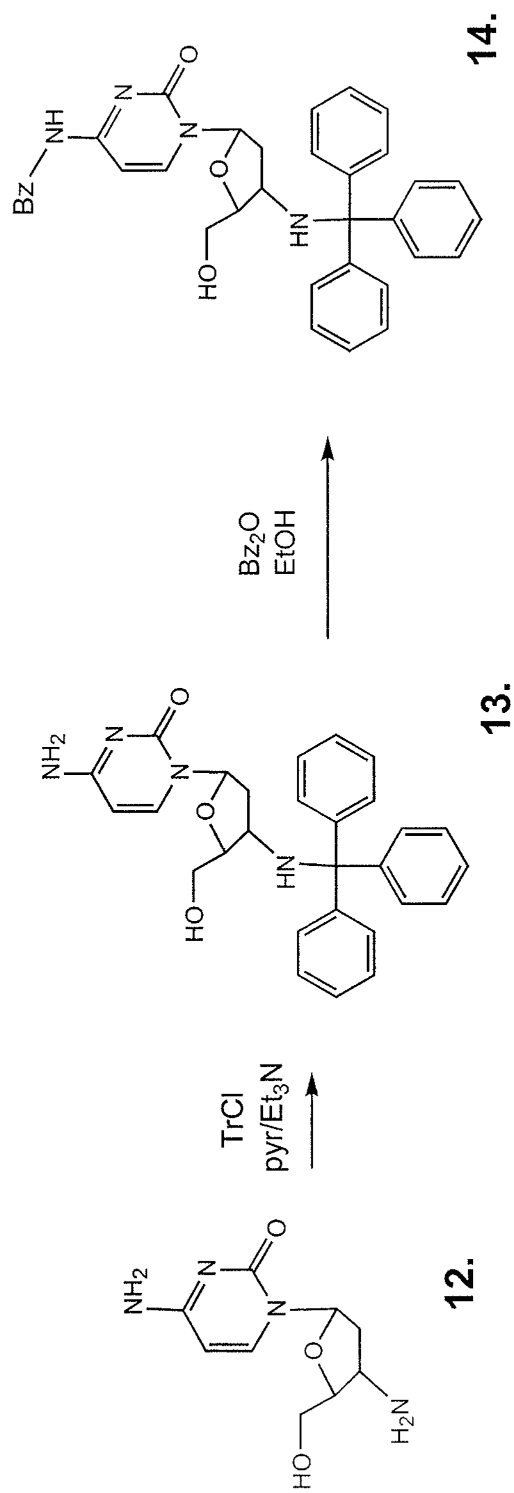
FIG. 2C shows a method for synthesis of 3'-amino cytidine monomer, in accordance with a further embodiment of the invention.

In another embodiment, such as illustrated in FIG. 2B, a more polar solvent, such as DMF, is used to solubilize the starting monomer 7, and the reaction scheme is otherwise similar to the "transient protection" scheme (using a TMS ether as the 5'-hydroxyl protecting group) shown for the adenosine monomer 1 in FIG. 1.

FIG. 2C illustrates an embodiment of a synthetic strategy, particularly applicable to cytidine monomers, in which 5'-hydroxyl protection is not employed. In this reaction scheme, following selective protection of the 3'-amino group of the monomer 12 with, for example, a trityl group, the exocyclic amino group of the base is reacted with an acyl anhydride, such as benzoyl anhydride. The solvent preferably contains an alcohol, which is believed to compete with and suppress reaction of the 5'-hydroxyl group. Examples include methanol, ethanol, and mixtures of these solvents with, for example, acetonitrile, DMF, or pyridine. In the reaction using benzoyl anhydride in ethanol or in 9:1 acetonitrile:methanol, as described in Example 4, little (<5%) of the 5'-benzoylated product was observed. The predominant 5'-hydroxyl monomer 14 can then be phosphitylated by standard methods.

In another embodiment, particularly applicable to adenosine or guanosine monomers, following selective protection of the 3'-amino group of the monomer with, for example, a trityl group, the exocyclic amino group of the base is protected with a dialkylformamidinyl, di(cycloalkyl)formamidinyl, or dibenzylformamidinyl group, preferably a dimethylformamidinyl group. The 5'-hydroxyl group, which is expected to remain substantially or fully unreacted during these steps, can then be phosphitylated by standard methods.

B3. Protection Strategies: T Monomer

In another aspect, the invention provides a method of preparing a thymidine monomer having a free 5'-hydroxyl group and a protected 3'-amino group. The synthetic strategy differs from that described above, in that the thymine base does not generally require protection under conditions of oligonucleotide synthesis. The starting material in this case is a 3'-amino-3'-deoxy thymidine monomer in which the 5'-hydroxyl group and 3'-amino group are unprotected, and the method comprises selectively reacting said 3'-amino group with a first protecting group, such that the 5'-hydroxyl group remains substantially unprotected.

As in the syntheses described above, a preferred protecting group for the 3'-amine is an acid labile group, such as a triarylmethyl group, or a group, such as Fmoc, which is labile to a basic amine reagent such as DBU. A trityl group is employed in the embodiment of FIG. 3.

The 5'-hydroxyl group can then be phosphitylated, as described e.g. in Example 5 below Note that this phosphitylation process is also applicable to any of the 5'-hydroxyl, 3'-amino-protected and base-protected monomers described above.

EXAMPLES

The following examples illustrate but are not intended to limit the invention. For example, reaction conditions, such as choice of solvent, catalyst (e.g. triethylamine or diisopropyl ethyl amine), reaction times, and reaction temperatures, can generally be varied from those exemplified below, according to the knowledge of one skilled in the art, using routine experimentation. In some cases, order of addition of reagents could be varied. Suitable solvents for the majority of these reactions, where not otherwise indicated, generally include polar aprotic solvents such as pyridine, DMF, acetonitrile, or mixtures thereof. Suitable temperatures are generally in the range of −10° C. to room temperature to about 55° C.

Example 1

Synthesis of $N^6$-benzoyl-3'-aminotrityl-2',3'-dideoxyadenosine from 3'-amino-2',3'-dideoxyadenosine

A. Method 1

Perbenzoylation Route (as Illustrated in FIG. 1, 1→2→3→6)

The starting monomer, 3'-amino-2',3'-dideoxyadenosine (1, 10 mmol), was coevaporated with dry pyridine, then suspended in 100 ml dry pyridine containing 6 eq. triethylamine, and the mixture was heated to 50° C. with stirring. Trityl chloride (1.1 eq.) was added, and stirring was continued for two hours at 50° C. The obtained clear solution containing the 3'-tritylated monomer 2 was cooled to 0° C., 5 eq. benzoyl chloride was added dropwise, and the reaction mixture was stirred for one hour and then poured into 100 ml of cold 5% sodium bicarbonate. The precipitated yellow gum was extracted with ethyl acetate, and the ethyl acetate solution evaporated. The resulting oil (3, having a benzoyl group at the 5'-hydroxyl and two at $N^6$ of the base) was dissolved in 50 ml pyridine:methanol:water 65:35:5 v/v/v, the solution was cooled to 0° C., and 50 ml 2M sodium hydroxide was added. After 25 min stirring at 0° C., the reaction mixture was neutralized with pyridinium hydrochloride, and the volume of the mixture was reduced by evaporation. After dilution with ethyl acetate, the organic layer was separated and washed with satd. sodium bicarbonate and evaporated in vacuo. The product was purified by silica gel flash column chromatography using methylene chloride:methanol 95:5 v/v solvent system. The isolated yield of product (6), having a free 5'-hydroxyl and monobenzoylated base, was 2.0 g (33.6%)

B. Method 2

Transient Protection Route (as Illustrated in FIG. 1, 1→2→6)

The starting monomer, 3'-amino-2',3'-dideoxyadenosine (1, 10 mmol), was converted to the 3'-protected monomer 2 as described above, i.e. by treatment with 1.1 eq. trityl chloride in dry pyridine containing 6 eq. triethylamine at 50° C.

The clear solution of 2 was cooled to 0° C., and 5 eq. chlorotrimethylsilane was added dropwise, followed by stirring for 30 min, producing a 5'-OTMS intermediate. Benzoyl chloride (5 eq) was then added dropwise, followed by stirring for two hours at room temperature, producing a monobenzoyl and/or dibenzoyl base protected intermediate.

The reaction mixture was cooled to 0° C., and 20 ml cold water was added, followed by 20 min stirring and addition of 20 ml conc. ammonium hydroxide. Stirring was continued for 30 min, and the solution was concentrated in vacuo. The oily residue was taken up in ethyl acetate and washed with satd. sodium bicarbonate, and the solution was dried and evaporated in vacuo. The product was purified as above by silica gel chromatography. Isolated yield of product (6) was 3.6 g (60.2%).

In subsequent procedures, DMF or DMF/pyridine, with added triethylamine, was used as solvent for the initial tritylation reaction, and the intermediate 2 was further reacted, using either Method A or Method B, to give the product 6 in about 70% yield. Yields were found to be somewhat improved by removal of triethylamine (e.g. by aqueous washings) prior to benzoylation, particularly when using Method A. This treatment was observed to prevent formation of a side product believed to result from ring opening of the adenine base. Formation of this side product was also eliminated by isolating the tritylated product 2 before further reaction.

C. Method 3

TBDMS Protection Route (as Illustrated in FIG. 1, 1→2→5→6)

The starting monomer, 3'-amino-2',3'-dideoxyadenosine (1, 10 mmol), was converted to the 3'-protected monomer 2 as described above, i.e. by treatment with 1.1 eq. trityl chloride in dry pyridine containing 6 eq. triethylamine at 50° C.

To the clear solution was added 2 eq. tert-butyldimethylsilyl chloride (TBDMS Cl), and stirring was continued overnight at room temperature. This solution (of the 3'-tritylamino-5'-TBDM silyloxy intermediate 4) was cooled to −5° C., and 3 eq. benzoyl chloride was added dropwise, following by stirring at room temperature for two hours, providing the $N^6$-dibenzoyl intermediate 5. The solution was concentrated in vacuo, and the oily residue was taken up in ethyl acetate, washed with satd. sodium bicarbonate, dried and evaporated in vacuo.

The oily residue obtained was dissolved in 100 ml THF, and 2 eq. TBAF (tetrabutylammonium fluoride) was added. The mixture was stirred overnight at room temperature. Ethyl acetate was added to the reaction mixture, and the solution was washed with sodium bicarbonate, 0.5 M sodium citrate (pH 4) and brine. The product was purified as above by silica gel chromatography to give 3.3 g (55.5%) of pure compound 6.

Example 2

Synthesis of $N^4$-benzoyl-3'-aminotrityl-2',3'-dideoxycytidine

The synthesis of $N^4$-benzoyl-3'-aminotrityl-2',3'-dideoxycytidine from 3'-amino-2',3'-dideoxycytidine can be carried out in a similar manner, using any of the above procedures, or in accordance with the method of Example 4, below.

Example 3

Synthesis of $N^2$-isobutyryl-3'-aminotrityl-2',3'-dideoxyguanosine from 3'-amino-2',3'-dideoxyguanosine (FIG. 2A)

The starting material, 3'-amino-2',3'-dideoxyguanosine (7, 2 g) was coevaporated with dry pyridine, then suspended in 100 ml dry pyridine and 6 eq. diisopropylethylamine. Tert-butyldimethylsilyl chloride (2 eq.) was added, producing a 5'-TBDM silyloxy intermediate. After 30 min stirring, 1.1 eq. of trityl chloride was added in two installments, and the stirring was continued overnight at room temperature. Two compounds were detected by TLC, the lower running, more abundant product 8 being the desired 5'-TBDMS-3'-aminotrityl-2',3'-dideoxyguanosine. The higher running, less abundant compound 9 is additionally tritylated at the base. The monotrityl compound 8 was isolated by silica gel chromatography using methylene chloride:methanol:triethylamine 94:5:1 v/v/v solvent system.

This product was coevaporated with dry pyridine and dissolved in 100 ml of pyridine. The solution was cooled to 0° C., and 1.1 eq. isobutyryl chloride was added, followed by stirring for 30 min. After quenching the reaction with methanol and evaporation in vacuo, the reaction was worked up from methylene chloride-sodium bicarbonate. The organic phase was dried over sodium sulfate and evaporated in vacuo. The oily residue (the fully protected monomer 10) was dissolved in 100 ml tetrahydrofuran, and 5 eq. tetrabutylammonium fluoride was added. The reaction mixture was stirred at room temperature overnight, then diluted with ethyl acetate, washed with sodium bicarbonate. After drying over sodium sulfate the solvent was evaporated in vacuo to give 2 g of the 5'-hydroxyl product 11 (46.1%).

In subsequent procedures, tritylation of 7 was carried out in DMF/pyridine at 50° C., and the side product 9 (<5%) was removed by precipitating the predominant product 8 from dichloromethane or water. The nucleotide base was protected using either the transient protection scheme of FIG. 2B or a peracylation reaction (analogous to Example 1A). The product 11 was isolated, after crystallization from $CH_3CN$, in yields of about 60% and 53%, respectively. Yields were also observed to improve when care was taken to avoid hydrolysis of the acyl chloride reagent.

Example 4

Synthesis of $N^4$-benzoyl-3'-aminotrityl-2',3'-dideoxycytidine from 3'-amino-2',3'-dideoxycytidine (as Illustrated in FIG. 2C)

The 3'-amino group of the starting material 12 was reacted with trityl chloride in 1:4 pyridine:DMF in the presence of triethylamine. The intermediate 13 was reacted with benzoyl anhydride in 9:1 $CH_3CN$:MeOH at 50° C. The desired product 14 was isolated, following silica gel chromatography, in 70% yield.

Example 5

Figure 3:
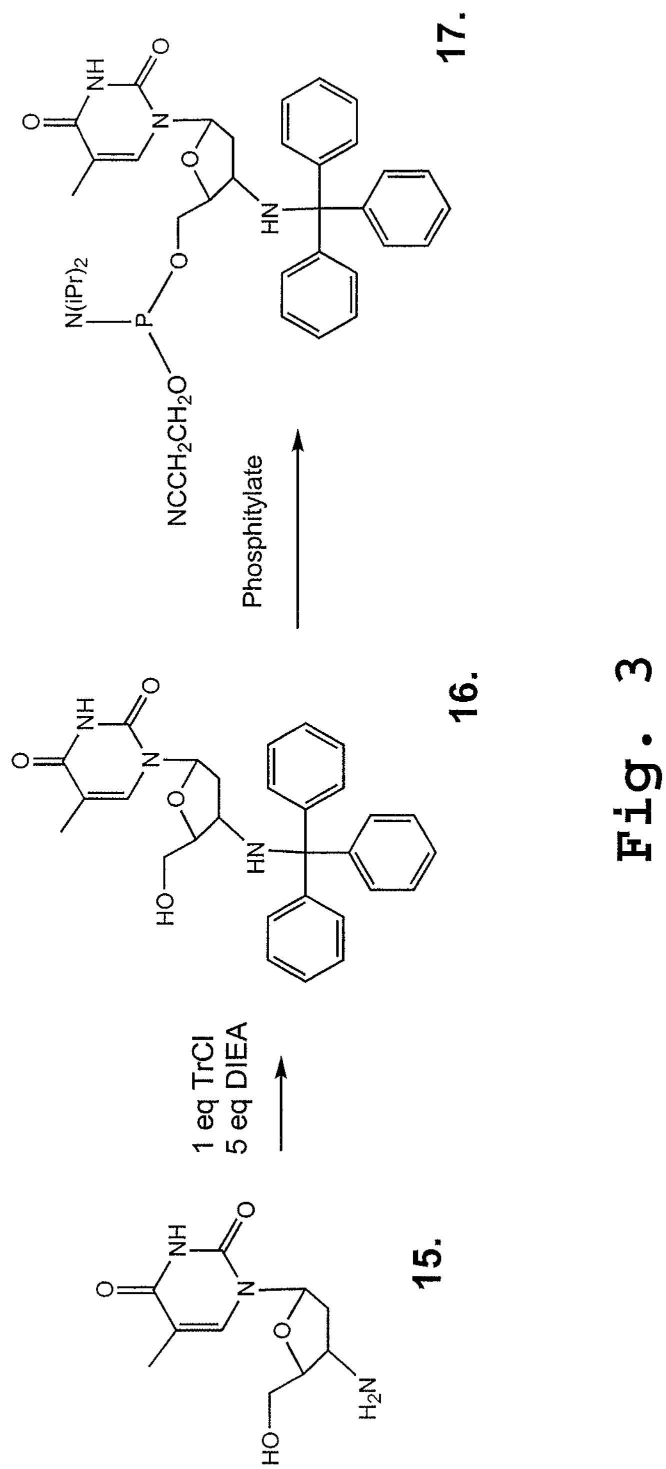
FIG. 3 shows an exemplary method for synthesis of a 3'-amino thymidine monomer, in accordance with a further embodiment of the invention.

Synthesis of 3'-aminotrityl-3'-deoxy-thymidine-5'-(2-cyanoethyl, N,N-diisopropyl)phosphoramidite from 3'-amino-3'-deoxythymidine, Followed by Phosphitylation (as Illustrated in FIG. 3)

The starting material, 3'-amino-3'-deoxythymidine (15, 1.3 g) was co-evaporated with dry pyridine, then dissolved in 30 ml dry pyridine. To this solution was added 5 eq. diisopropylethylamine or triethylamine, followed by 10 min stirring and addition of 1 to 1.1 eq. trityl chloride. The reaction mixture was stirred at room temperature overnight (or, alternatively, at 50° C. for 1 hour). After disappearance of the starting material by TLC, the reaction was quenched with methanol and the solution evaporated in vacuo. The oil obtained was dissolved in methylene chloride, washed with satd. sodium bicarbonate, dried over sodium sulfate and concentrated. Methylene chloride-hexane precipitation gave 2.2 g (85%) of the product 16 as a white powder.

The product 16 (1.7 g) was coevaporated with dry pyridine and dissolved in 100 ml of dry methylene chloride. To this solution was added 4 eq. of diisopropylethylamine, followed by 1.2 eq. 2-cyanoethyl-N,N-diisopropylchlorophosphoramidite. The reaction was monitored by TLC, and after the disappearance of the starting material the solution was washed with satd. sodium bicarbonate, dried over sodium sulfate and evaporated in vacuo. The product was purified by silica gel flash chromatography using methylene chloride: triethylamine 10:1 v/v solvent system to yield 2 g (83.3%) of the phosphitylated protected monomer 17 as a solid foam. The overall yield of the procedure was 70.8%.

While the invention has been described with reference to specific methods and embodiments, it will be appreciated that various modifications may be made without departing from the invention.

It is claimed:

1. A 2,3'-dideoxy, 3"-amino adenosine monomer or a 2',3'-dideoxy, 3'-amino guanosine monomer wherein the 2'-group of the monomer is hydrogen, and the monomer has a 3'-amino group protected with an acid-labile group or a fluorenylmethoxycarbonyl group or a derivative of a fluorenylmethoxycarbonyl group; a nucleoside base which is protected with a dialkyl-, di(cycloalkyl)- or di(aralkyl)-formamidinyl group; and an unprotected 5'-hydroxyl group.

2. The monomer of claim 1, wherein said alkyl is $C_1$-$C_4$ alkyl and said cycloalkyl is $C_5$-$C_6$ cycloalkyl.

3. The monomer of claim 1, wherein said acid labile protecting group is a triarylmethyl group.

4. The monomer of claim 1, wherein said nucleoside base is protected with a dimethylformamidinyl group or a dibenzylformamidinyl group.

5. The monomer of claim 1, wherein said nucleoside base is protected with a dimethylformamidinyl group.

6. The monomer of claim 1, wherein the 3'-amino group is protected with a fluorenylmethoxycarbonyl group or a derivative of a fluorenylmethoxycarbonyl group.

7. A 2',3'-dideoxy adenosine monomer or a 2',3'-dideoxy, 3'-amino guanosine monomer wherein the 2'-group of the monomer is hydrogen and the monomer has a 3'-amino group protected with an acid-labile group or a fluorenylmethoxycarbonyl group or a derivative of a fluorenylmethoxycarbonyl group; a nucleoside base which is protected with a dialkyl-, di(cycloalkyl)- or di(aralkyl)-formamidinyl group; and a 5'-O-(2-cyanoethyl-N,N-diisopropylamino)phosphoramidite group.

* * * * *

UNITED STATES PATENT AND TRADEMARK OFFICE

CERTIFICATE OF CORRECTION

PATENT NO. : 8,748,593 B2
APPLICATION NO. : 12/341750
DATED : June 10, 2014
INVENTOR(S) : Sergei M. Gryaznov et al.

It is certified that error appears in the above-identified patent and that said Letters Patent is hereby corrected as shown below:

In the claims,

At column 14, claim number 1, line number 15, delete "2,3′-dideoxy, 3″-amino" and replace with "2′,3′-dideoxy, 3′-amino".

At column 14, claim number 7, line number 35, delete "2′,3′-dideoxy adenosine" and replace with "2′,3′-dideoxy, 3′-amino adenosine".

Signed and Sealed this
Ninth Day of February, 2016

Michelle K. Lee
*Director of the United States Patent and Trademark Office*